(12) United States Patent
Domeier (10) Patent No.: US 7,373,800 B2
(45) Date of Patent: May 20, 2008

(54) FRICTION TEST APPARATUS AND METHOD

(76) Inventor: Joachim Domeier, 524 Lakeview Ave., Ann Arbor, MI (US) 48103

( * ) Notice: Subject to any disclaimer, the term of this patent is extended or adjusted under 35 U.S.C. 154(b) by 0 days.

(21) Appl. No.: 10/996,255

(22) Filed: Nov. 23, 2004

(65) Prior Publication Data

US 2005/0072208 A1 Apr. 7, 2005

Related U.S. Application Data

(62) Division of application No. 10/439,405, filed on May 16, 2003, now Pat. No. 6,857,306.

(60) Provisional application No. 60/381,479, filed on May 17, 2002.

(51) Int. Cl.
*G01N 3/56* (2006.01)
(52) U.S. Cl. .................. 73/9; 73/10; 73/53.06
(58) Field of Classification Search .............. 73/9, 73/10, 53.05, 53.06
See application file for complete search history.

(56) References Cited

U.S. PATENT DOCUMENTS

| | | | | |
|---|---|---|---|---|
| 3,302,447 A | * | 2/1967 | Mertwoy et al. | 73/10 |
| 3,380,288 A | * | 4/1968 | Bradley | 73/9 |
| 3,939,690 A | * | 2/1976 | Kuss et al. | 73/9 |
| 4,228,674 A | * | 10/1980 | Mertwoy | 73/10 |
| 5,275,258 A | * | 1/1994 | Bousseau | 184/6.4 |
| 5,388,442 A | * | 2/1995 | Kumar et al. | 73/10 |
| 5,863,872 A | * | 1/1999 | Garmier | 508/491 |
| 6,477,885 B1 | * | 11/2002 | Sekine et al. | 73/10 |
| 2003/0101793 A1 | * | 6/2003 | Evans | 73/9 |

FOREIGN PATENT DOCUMENTS

GB 2183347 A * 6/1987

OTHER PUBLICATIONS

ASTM 2783-88 (Standard Test Method for Measurement of Extreme-Pressure Properties of Lubricating Fluids (Four-Ball Method), Dec. 1988.*
Boerlage et al. Engineering "Four-Ball Top for Testing the Boundary Lubricating Properties of Oils under High Mean Pressures", Jul. 2, 1937, vol. CXLIV.*
http://web.archive.org/web/20000531132119/http://www.labkorea.com/products/falex/4.htm Archived on May 31, 2000.*

* cited by examiner

*Primary Examiner*—Michael Cygan
(74) *Attorney, Agent, or Firm*—Price, Heneveld, Cooper, DeWitt & Litton, LLP (57) ABSTRACT

A friction test apparatus includes a base structure and a receptacle secured to the base structure. At least three lower friction surfaces are positioned in the receptacle. The friction test apparatus includes a motor having a rotatable shaft providing powered rotation of the shaft. An upper friction surface is positioned on the shaft in contact with the at least three friction surfaces in the receptacle. The receptacle includes a fluid inlet and a fluid outlet to permit a fluid in the receptacle to be changed.

7 Claims, 7 Drawing Sheets

FRICTION TEST APPARATUS AND METHOD

CROSS-REFERENCE TO RELATED APPLICATIONS

The present application is a divisional of U.S. patent application Ser. No. 10/439,405, filed May 16, 2003, now U.S. Pat. No. 6,857,306 which claims the benefit of U.S. Provisional Application No. 60/381,479, entitled FOUR-BALL WEAR TEST MACHINE, filed on May 17, 2002, the entire contents of which are incorporated herein by reference.

BACKGROUND OF THE INVENTION

Figure 1:
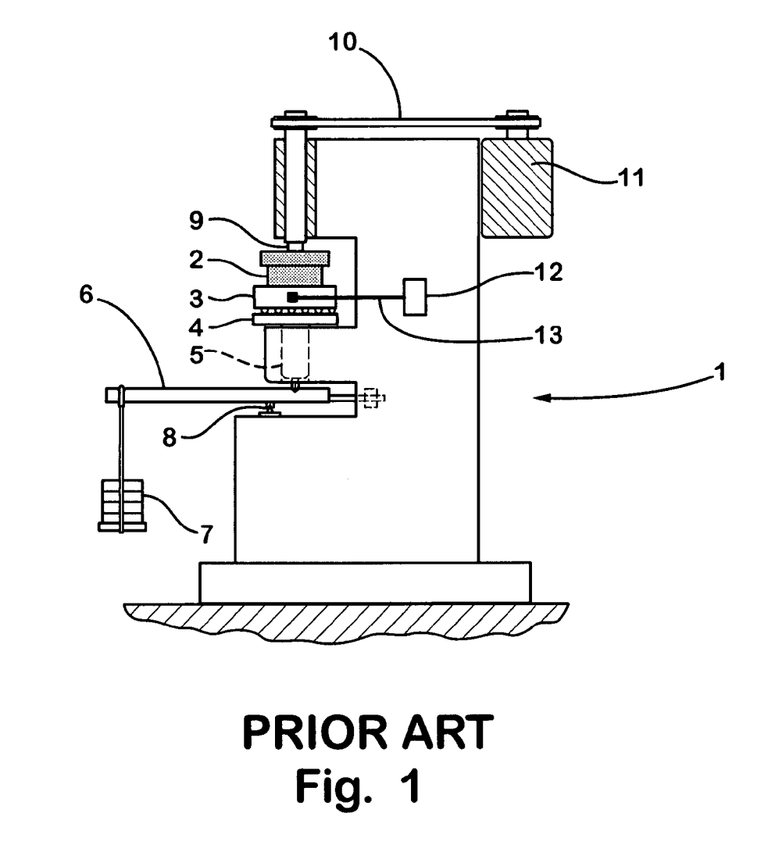
FIG. 1 is a partially schematic side elevational view of a prior art four-ball tester including a lever arm for generating a test load.

Various four-ball test machines have been developed to evaluate the friction and wear characteristics of lubricants such as motor oils, hydraulic oils, cutting fluids, greases, solid lubricants or the like. Existing four-ball testers can also be used to evaluate the friction wear characteristics of bearing materials. In this case, the test balls themselves would be made of the material to be tested, and the same lubricant fluid would be utilized for the various varying materials to be tested. Known four-ball testers include a test cup with three steel balls positioned inside the test cup. The steel balls are held very tightly together by a conical ring that is secured via threaded fasteners to lock the balls in place. A typical four-ball test machine utilizes three steel balls that are ½ inch in diameter. A test fluid is placed inside the cup covering the three balls. With reference to FIG. 1, the test cup 2 is then positioned in a four-ball tester 1. The prior art four-ball tester illustrated in FIG. 1 includes a heater block 3 to heat the test cup 2 and fluid. As described in more detail below, a thrust bearing 4 supports heater block 3 on support column 5. Weights 7 are supported by lever arm 6 which pivots about a pivot 8 to push upwardly on the support column 5. A rotating shaft or spindle 9 has a fourth test ball at the end thereof (not shown) that contacts the three test balls in the test cup 2. The shaft 9 is connected to an electric motor 11 via a belt 10 for powered rotation of the shaft 9.

The amount of force pushing the three balls in the test cup 2 against the ball on the rotating spindle 9 can be varied by changing the weights 7. Typical lever arms 6 have a 10-to-1 ratio such that a four-kilogram weight 7 causes the bottom three balls in the test cup 2 to push up against the rotating top ball on spindle 9 with a force of 40 kg.

During a typical four-ball wear test 3 new test balls are placed into a clean test cup 2 and clamped securely in place above the heater block 3. The test fluid is then added to the test cup 2, and a new test ball is secured to the shaft 9. Shaft 9 includes a chuck (not shown) that secures the upper test ball to the shaft 9. During the test, the heater block 3 is turned on, and the temperature of the test fluid in the test cup 2 is monitored. When the test fluid reaches the test temperature, the load is applied and the motor 11 is actuated to thereby rotate the spindle 9.

A common ASTM test method utilizes a load of 40 kg, and is run at 1200 rpm at 75° C. for one hour. At the end of the test run the motor is stopped, the heater is turned off, the load is removed, and the test cup 2 is taken off the tester 1.

The thrust bearing 4 under the heater 3 allows the heater 3 and test cup 2 to rotate freely and also to move horizontally because one of the races of the thrust bearing 4 is replaced with a flat hard steel surface. With this arrangement, the cup 2 can freely move in any direction and center itself under the top rotating ball that is secured to the shaft 9. The top ball contacts each of the three bottom balls in the test cup 2. Upon rotation of the top ball, a force is transmitted to the test balls in the test cup 2, tending to rotate the test cup 2. However, a load cell 12 is contacted to the heater block 3 via a small chain 13 that prevents rotation of the heater block 3 and test cup 2. The load cell 12 is utilized to measure the rotational force acting on the test cup 2, and to thereby calculate the coefficient of friction.

Upon completion of the test, the test cup is removed from the tester 1, and the test lubricant is drained. The cup 2 with the three bottom test balls still locked in place is placed under a microscope to measure the wear scars. The wear scars result from the top ball rotating against each of the bottom three balls under the test load. The wear scars are measured for each of the bottom three balls. In general, each of the three bottom balls will have a wear scar that is very similar in size and shape to the other two lower test balls. A measurement is made with a microscope of each wear scar diameter, in both the vertical and horizontal direction. A total of six measurements are taken, two for each ball, and then the average of the six readings is considered to be the wear scar diameter for a given test fluid under a specific test method.

The torsional forces that have been measured with the load cell 12 can also be averaged out over the test period and can be used to calculate the average coefficient of friction for a given test fluid under specific test conditions. Two characteristics of a lubricant can be determined in this way: 1) the coefficient of friction of the fluid; and 2) the amount of wear that occurred in the presence of the test fluid under given test conditions.

Upon completion of a test utilizing a first test fluid, another lubricant or a modified formula of the same lubricant, can be run under the same test conditions, and the friction wear characteristics can be compared with those of the first lubricant.

As discussed above, the four-ball test provides information concerning: 1) the average wear-scar diameter; and 2) the average coefficient of friction, or a full friction trace for the test duration. The type of signal processing system attached to the tester will determine whether the average coefficient of friction or a full friction trace is produced by the test.

One frequent use for four-ball testers is as a quality control check for hydraulic fluids. Such tests commonly utilize a 40 kg load at 1200 rpm and 75° F. with a one hour duration. Other applications for four-ball tests include quality control tests for automatic transmission fluids. Four-ball tests are also used for quality control for many other automotive or other fluids such as brake fluids, motor oils, gear oils, torque fluids, mineral based cutting oils, water based cutting oils, and other fluids. A variety of fluids or semi-fluids for which wear and friction value are of importance can be tested using four-ball friction wear testing. The wear scar diameter and friction value can also be utilized to determine if a material has a proper composition. In such testing, the test balls are made of the material to be tested, and a lubricant having known properties is utilized.

Four-ball test equipment can also be utilized to formulate the various fluids discussed above. For example, if a fluid includes a component that is no longer available, a fluid including a replacement component can be tested to determine if the new formulation has beneficial or detrimental friction and wear characteristics. Still another use for four-ball testers is to monitor the condition of fluids during use to determine when they are no longer acceptable, or when an additive to the fluid is needed.

Figure 2:
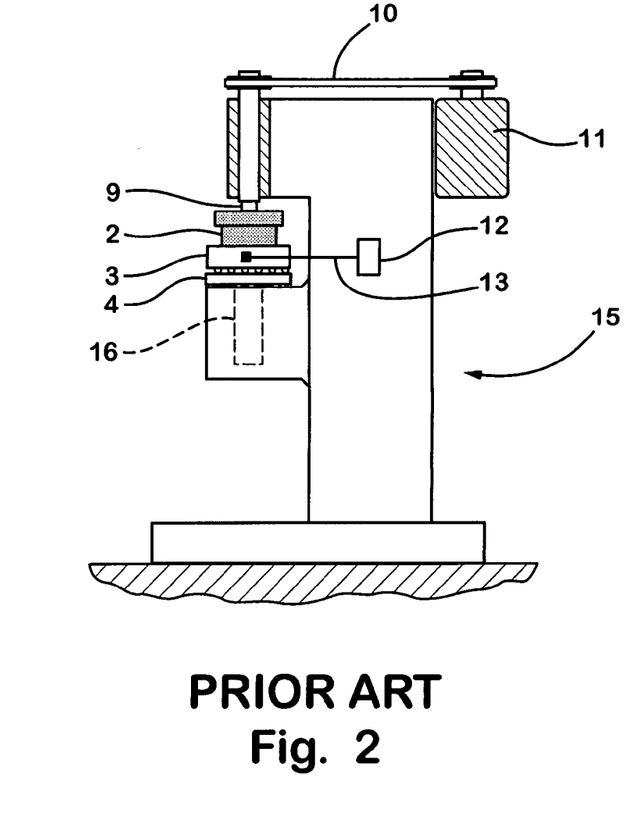
FIG. 2 is a partially schematic side elevational view of a prior art four-ball tester including a pneumatic cylinder for providing a test load.

As discussed above in connection with FIG. 1, one known type of four-ball tester utilizes a lever arm and weight to generate force on the test balls. Another type of known four-ball tester 15 is illustrated in FIG. 2. The four-ball tester 15 illustrated in FIG. 2 includes a test cup 2, heater block 3, spindle 9, belt 10, electric motor 11, load cell 12, and chain 13 arranged in substantially the same manner as discussed above in connection with the tester 1 of FIG. 1. However, rather than a lever arm 6, the support column 16 of the four-ball tester 15 of FIG. 2 is connected to a pneumatic cylinder (not shown) that pushes upwardly on the support column 16 to apply the test load. The test load of the tester 15 can be adjusted by simply turning the pressure regulator knob to the desired pressure setting. Also, the thrust bearing 4 of tester 15 may be replaced with an air bearing. Such air bearings are utilized in an attempt to provide a very low friction support that provides a more accurate friction reading.

However, existing four-ball testers such as those illustrated in FIGS. 1 and 2 suffer from numerous drawbacks. For example, it is generally not possible to determine the exact actual load on the test balls. The lever type testers may have frictional losses at the fulcrum points, and also in the guide tub. Also, the load arm needs to be adjusted to balance it without any load on it. The load arm must also be adjusted to be perfectly level during testing. These variables can result in inaccurate data if the test setup is not thoroughly checked.

Pneumatic four-ball testers (FIG. 2) also suffer from various drawbacks. For example, the pneumatic loading system needs dry air. Also, the accuracy of the load will be compromised if the pressure meter is not accurate. Also, pneumatic cylinders may "stick-slip" causing a force variation. In an effort to alleviate the stick-slip phenomenon, a free-floating or non-sealing cylinder has been utilized. This arrangement allows air to pass around the piston, between the piston and cylinder wall so that the piston is always loose inside the cylinder. This arrangement provides a constant flow of air through the air cylinder, resulting in various problems. Also, the piston in such free-floating arrangement may angle slightly sideways and lock against the walls of the cylinder.

Furthermore, the air bearing utilized with such four-ball testers may also suffer from various drawbacks. For example, because the air bearing is on top of the air cylinder that applies the load, the pressure of the air bearing needs to be higher than the pressure applied by the air cylinder. This may result in a higher load than expected. Also, air bearings may allow the test cup to tilt slightly, resulting in uneven wear scars and unreliable test results.

Accordingly, a four-ball tester alleviating the problems of existing arrangements would be desirable.

SUMMARY OF THE INVENTION

One aspect of the present invention is a friction test apparatus including a base structure and a receptacle secured to the base structure. At least three lower friction surfaces are positioned in the receptacle. The friction test apparatus includes a motor having a rotatable shaft providing powered rotation of the shaft. An upper friction surface is positioned on the shaft in contact with the at least three friction surfaces in the receptacle. The receptacle includes a fluid inlet and a fluid outlet to permit a fluid in the receptacle to be changed.

These and other features, advantages, and objects of the present invention will be further understood and appreciated by those skilled in the art by reference to the following specification, claims, and appended drawings.

DETAILED DESCRIPTION OF PREFERRED EMBODIMENT

Figure 3:
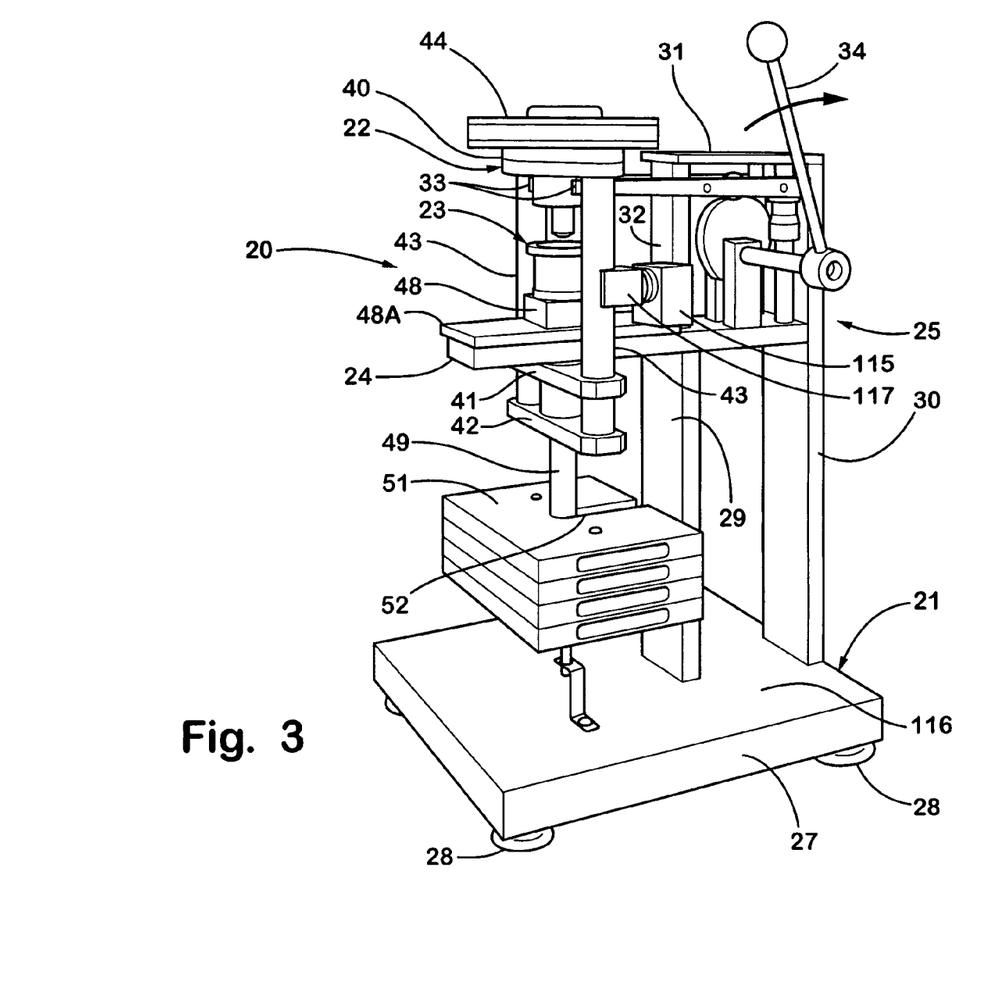
FIG. 3 is a perspective view of a four-ball test apparatus according to one aspect of the present invention.

For purposes of description herein, the terms "upper," "lower," "right," "left," "rear," "front," "vertical," "horizontal," and derivatives thereof shall relate to the invention as oriented in FIG. 3. However, it is to be understood that the invention may assume various alternative orientations and step sequences, except where expressly specified to the contrary. It is also to be understood that the specific devices and processes illustrated in the attached drawings and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

With reference to FIG. 3, a four-ball test apparatus 20 according to the present invention includes a base assembly 21, a motor/weight assembly 22, a test cup 23 that is supported on a horizontal support member 24 of base assembly 21, and a lift assembly 25 that raises the motor/weight assembly 22 out of engagement with the test cup 23 between tests. As described in more detail below, all of the weight of the motor/weight assembly is supported by an upper test ball on spindle 46 that contacts the lower test balls in test cup 23. The four-ball test apparatus of the present invention thereby ensures that all frictional forces measured by the load cell are due to the frictional engagement between the upper test ball and the lower test balls, and eliminates potential errors caused by thrust bearings or the like present in prior four-ball test arrangements.

The base assembly 21 includes a base plate 27 having feet 28 to support the four-ball test apparatus 20 on a worksurface 28. Front and rear vertical support members 29 and 30, respectively, are secured to the base plate 27, and extend vertically upwardly. The horizontal support member 24 is secured to the vertical members 29 and 30. An upper cross-member 31 is secured to intermediate vertical member 32. As described in more detail below, a pair of lift members 33 can be shifted vertically by routing handle 34 of lift assembly 25 to thereby lift the motor/weight assembly 22 out of engagement with the test cup 23 between tests for set up purposes, and the like.

Figure 4:
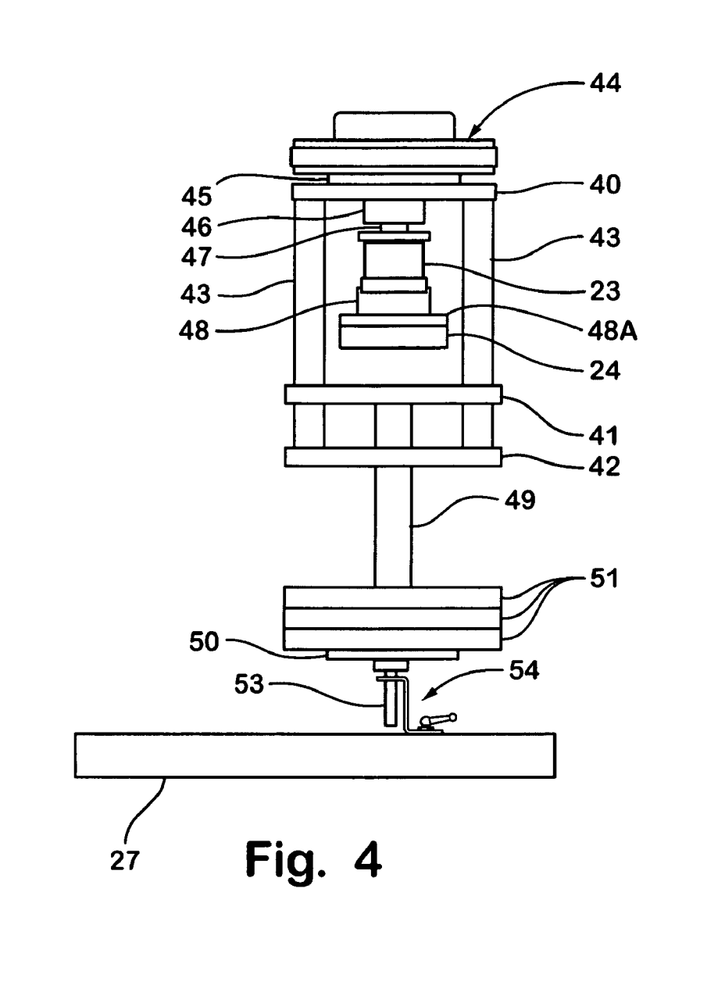
FIG. 4 is a partially fragmentary front view of the four-ball test apparatus of FIG. 3.

The motor/weight assembly 22 includes an upper plate 40 and lower plates 41 and 42. A pair of vertical support members 43 are rigidly secured to the upper plate 40 and the lower plates 41 and 42. The vertical support members 43 are spaced apart, such that the support member 24 extends between the vertical supports 43 (see also FIG. 4). An electric motor 44 is secured to the upper plate 40 by a mounting portion 45. The electric motor 44 rotates spindle 46 and chuck 47. As described in more detail below, the chuck 47 holds the upper test ball 73 of the four balls utilized in the four-ball test apparatus 20. Test cup 23 may be positioned on a heater block 48 and heater block 48 may be supported on an insulating pad 48A. Due to the relatively large contact area between the test cup 23 and heater block 48, the frictional forces prevent rotation of cup 23 during testing and no clamp or the like is normally required to secure cup 23.

Figure 6:
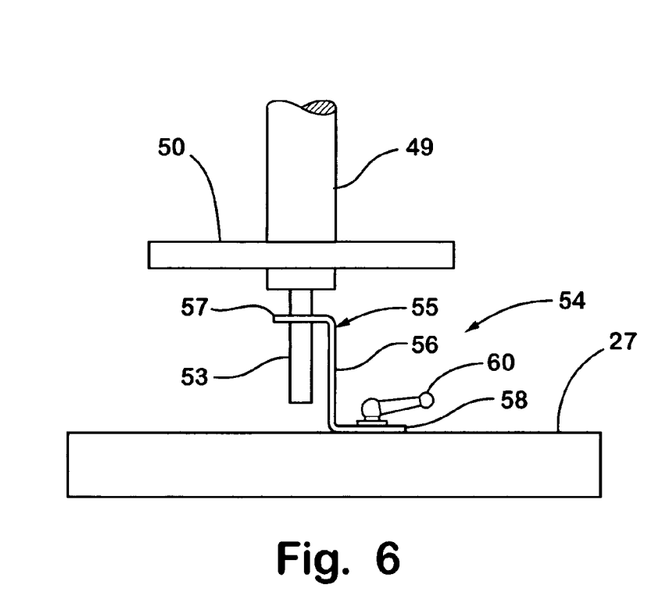
FIG. 6 is a partially fragmentary view illustrating the anti-swing guide of the four-ball test apparatus of FIG. 3.
Figure 7:
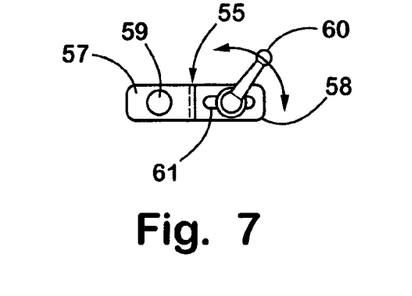
FIG. 7 is an enlarged view of the anti-swing apparatus of FIG. 6 from another angle.

The motor/weight assembly 22 further includes a lower vertical member 49 that is secured to the lower plates 41 and 42 and extends downwardly therefrom towards the base plate 27. A support member such as plate 50 is secured to the lower end of vertical member 49 to thereby support weights 51. Weights 51 are flat plate members having a slot 52 to provide clearance for the vertical member 49 such that the center of gravity of the weights 51 can be positioned at or near the center line of vertical member 49. An extension 53 at the lower end of vertical member 49 engages an anti-swing assembly 54 to prevent swinging of motor/weight assembly 22. With further reference to FIGS. 6 and 7, the anti-swing assembly 54 includes a bracket 55 that is generally Z-shaped including a vertical portion 56, an upper horizontal portion 57, and a lower horizontal portion 58. Upper horizontal portion 57 of bracket 55 includes a clearance opening 59 that receives the extension 53 to prevent swinging motion of the motor/weight assembly 22. A locking lever 60 extends through an elongated slot 61 in lower horizontal portion 58 of bracket 55, and selectively clamps the bracket 55 to the base plate 27. During setup, the locking lever 60 is first released, such that the bracket 55 can translate along slot 61, and can also rotate. The motor/weight assembly 22 will hang in a vertical position due to gravity. Once the motor/weight assembly 22 has reached the stable, vertical configuration, the lock lever 60 engaged, and the bracket 55 is clamped to the base plate 27. Because the opening 59 has a somewhat larger diameter than extension 53, the anti-swing assembly 54 positions the motor/weight assembly 22 without causing friction that would otherwise cause errors in the test measurements of the friction in the test cup 23. Lock lever 60 is preferably a rotating, threaded member or a cam type lock lever (not shown).

Figure 5:
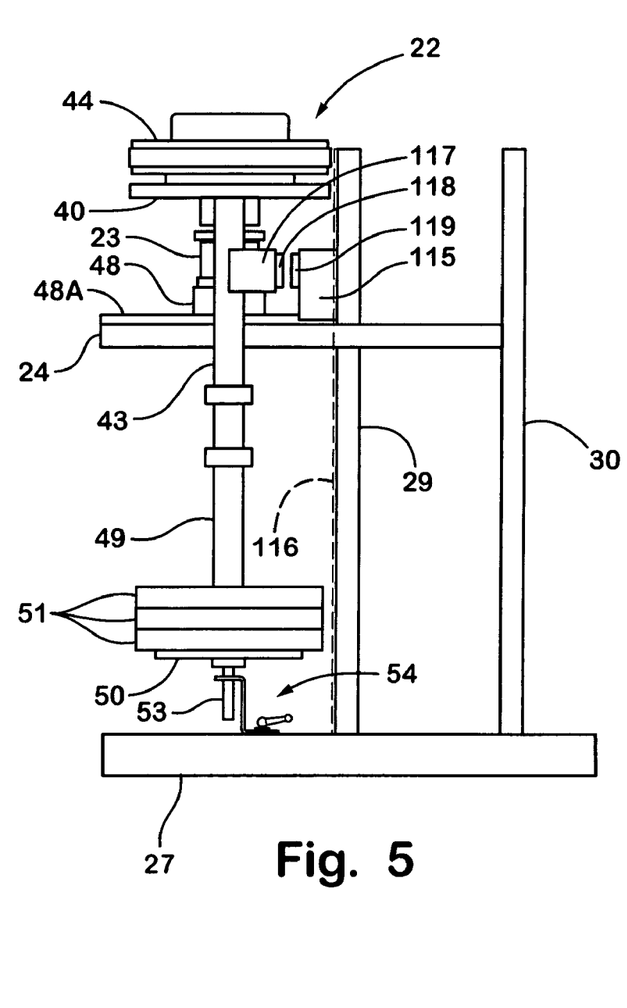
FIG. 5 is a partially fragmentary side elevational view of the four-ball test apparatus of FIG. 3.

With reference to FIGS. 3 and 5, a load cell 115 is secured to the horizontal support member 24, and is interconnected with the motor/weight assembly 22 to measure the torque generated by the friction at the contact point between the upper test ball 73 and the lower test balls 83. A relatively thin cover or face plate 116 may be secured to the front vertical member 29, and the load cell 115 may be secured to the cover 116. Alternately, load cell 115 may be mounted to the support member 24. The load cell 115 is positioned at the same height as the contact points between upper test ball 73 and lower test balls 83. In a preferred embodiment, a first magnet 118 is secured to the vertical support member 43 of motor/weight assembly 22 by a mounting bracket member 117, and a second magnet 119 is secured to the load cell 115. The magnets 118 and 119 are oriented such that the magnets repel one another, thereby transmitting the force from the motor/weight assembly 22 to the load cell 115 without physical contact. This arrangement prevents errors in the force measured that could otherwise result from friction or the like generated by a conventional mechanical interconnection. Magnets 118 and 119 may also be eliminated, such that direct contact occurs. Alternately, the load cell 115 could be interconnected to the motor/weight assembly 22 via a conventional mechanical interconnection such as a line, chain, or the like as described above in connection with FIGS. 1 and 2 if the load cell 115 is mounted on the other side of the spindle 46.

Figure 8:
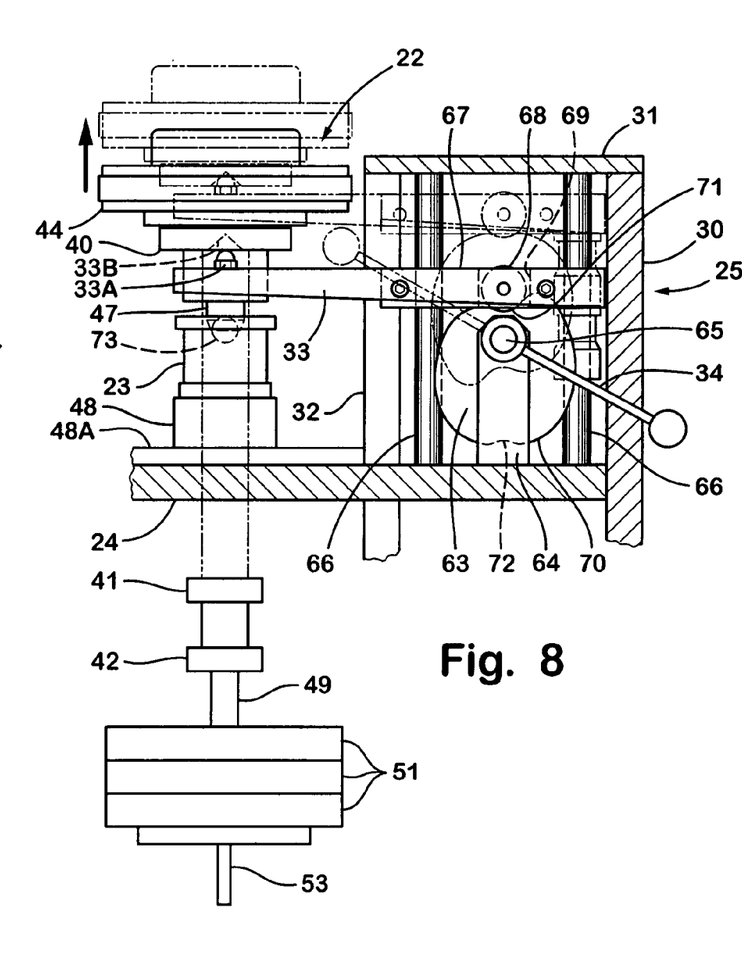
FIG. 8 is a partially fragmentary side elevational view illustrating the lift mechanism.

With further reference to FIG. 8, the lift assembly 25 includes a cam 63 that is pivotally mounted between a pair of upright support members 64. The cam 63 and handle 34 are both fixed to a shaft 65 that is rotatably mounted to the upright support 64. In a preferred embodiment, four vertical shafts 66 extend between the horizontal support member 24 and the upper cross-member 31. Alternately, as shown in FIG. 3, two shafts 66 may be utilized. A horizontal plate 67 extends between and rigidly interconnects the elongated lift members 33. A cam follower or roller 68 is rotatably mounted in a clearance opening 69 in plate 67, and is positioned to rotatably engage the outer surface 70 of cam 63. The cam outer surface 70 includes a first concave portion 71, and a second concave portion 72. The first concave portion 71 is positioned closer to the center line of shaft 65 than is second concave portion 72. Thus, the lift members 33 are positioned in a lower position as illustrated in FIG. 8 when the cam follower 68 engages the first concave portion 71 as illustrated in FIG. 8. In this position, the lift members 33 are disengaged from the plate 40 of the motor/weight assembly 22, such that the entire weight of the motor/weight assembly 22 is supported by the test ball 73 which engages the lower test balls 83 (see also FIG. 9) in the test cup 23. To raise the motor/weight assembly 22, the handle 34 is rotated until the second concave portion of the cam 63 engages the cam follower 68. This raises the lift members 33 until they engage plate 40 to thereby lift motor/weight assembly 22 to the upper, raised position indicated in dashed lines in FIG. 8. In the raised position, test ball 73 mounted in chuck 47 is out of engagement with the test balls in the test cup 23 and the weight of the motor/weight assembly is carried by lift members 33. The test cup and other test apparatus can then be adjusted or changed as required. Castle nuts 33A on lift members 33 engage openings or depressions 33B in plate 40 to thereby position motor/weight assembly 22 when lifted.

Figure 9:
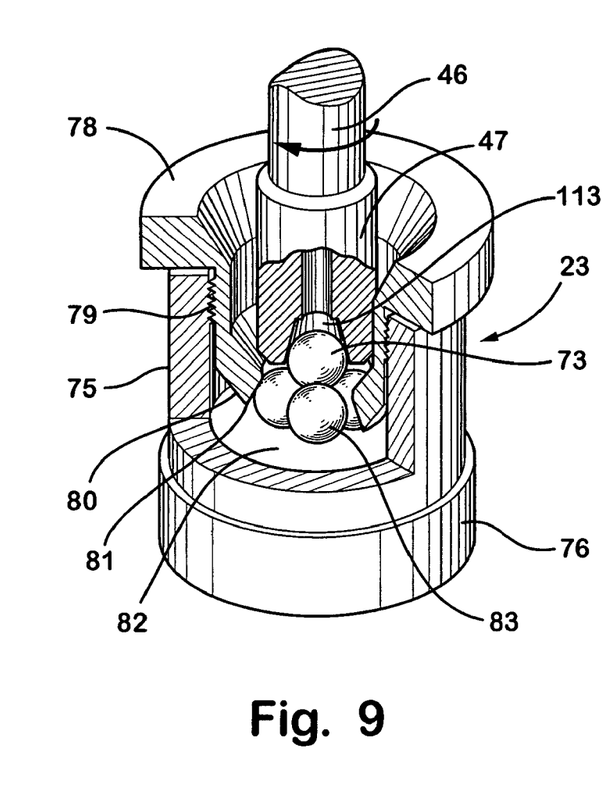
FIG. 9 is a partially fragmentary perspective view of a test cup that can be used with the four-ball test apparatus of FIG. 3.

With further reference to FIG. 9, the test cup 23 includes an outer cup shaped member 75 having a knurled base portion 76. An inner test cup member 78 is removably connected to the outer member 75 via threads 79. The test cup member 78 includes a lower flange 80 that extends inwardly and forms an edge surface 81. Three lower test balls 83 are positioned in the test cup 23, and are tightly clamped against the lower surface 82 of outer cup-shaped member 75. Lower surface 82 is tapered, and has a shallow cone shape. During setup, the lower test balls 83 are positioned in the outer member 75, and the inner member 78 is threaded into the outer member 75 until the edge 81 contacts the test balls 83 and tightly clamps them against the lower surface 82 of outer member 75. This clamping action prevents movement of the lower test balls 83 within the test cup 23 such that sliding contact occurs between the upper test ball 73 and lower test balls 83. Because the entire weight of the motor/weight assembly 22 is supported by the contact of the upper test ball 73 on the lower test balls 83, the four-ball test apparatus of the present invention ensures that no additional friction occurs, thereby ensuring that very accurate measurements of the friction between the upper test ball 73 and the lower balls 83.

Because the test cup of the present four-ball test apparatus 20 is rigidly secured to the support member 24, additional instruments or other connections can be made to the test cup itself without introduction of errors that would occur in existing test cup designs wherein the test cup "floats" on a thrust bearing or the like.

Figure 10:
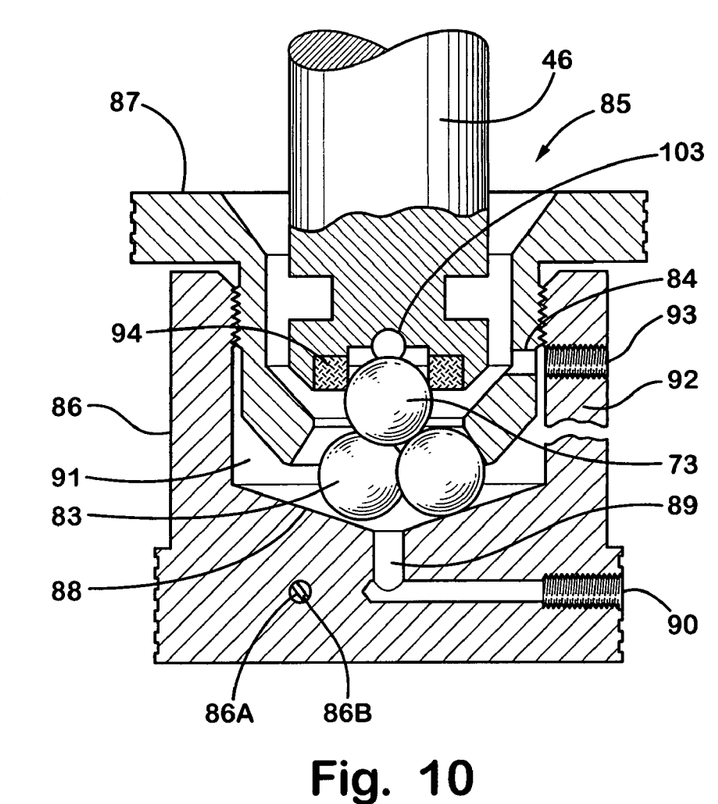
FIG. 10 is a cross-sectional view of another embodiment of a test cup that can be used with the four-ball test apparatus of FIG. 3.

With reference to FIG. 10, a test cup 85 according to another embodiment of the present invention includes an inner member 87 that threadably engages an outer cup shaped member 86 to clamp lower test balls 83 in substantially the same manner as described above in connection with the test cup 23 of FIG. 9. The outer member 86 includes a tapered lower surface 88 having a generally shallow conical shape. The conical shape of surface 88 causes test balls 83 to be pushed into tight contact with one another. A fluid passageway 89 is positioned at the center of the conical surface 88, and permits fluid flow through opening 90 into the interior 91 of outer member 86 through the passageway 89. A second threaded opening 93 extends through side wall 92 of outer member 86, and also permits flow of fluid out of the interior 91 of outer member 86. One or more openings 84 through the sidewall of inner member 87 at or above the height of opening 93 ensure that the test fluid fills inner member 87 and covers the test balls without exiting directly through opening 93 by siphoning as would occur if opening 84 were not present. A ring 94 made of a ceramic material secures the upper test ball 73 to the spindle 46 and also thermally insulates spindle 46. If the test ball 73 does become stuck in ring 94, a pin or the like can be driven through cross bore 103 to dislodge the test ball 73. A thermocouple 86A can be positioned in opening 86B to measure the temperature of the test cup 85 and test fluid in the cup.

Figure 11:
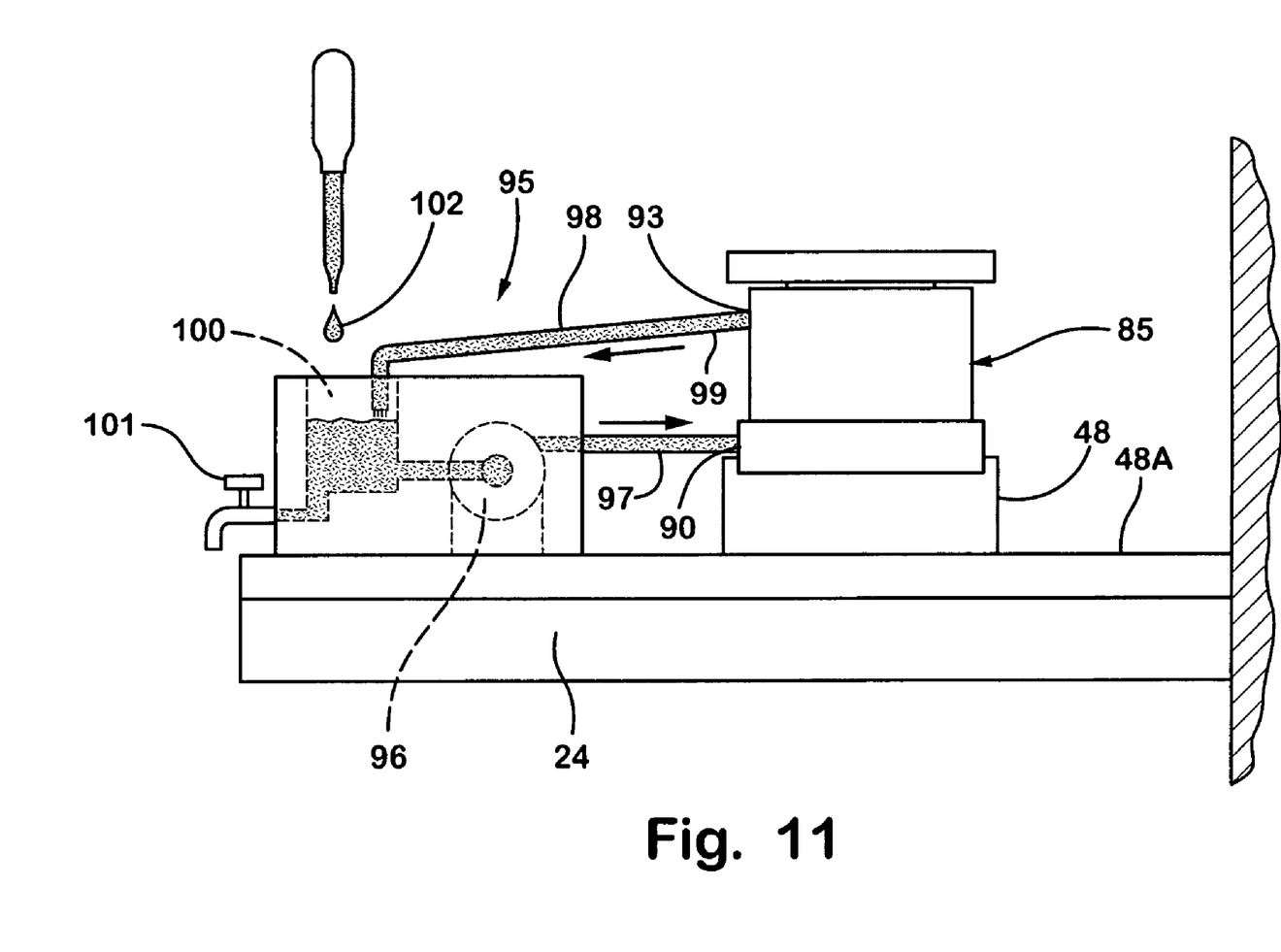
FIG. 11 is a partially schematic view wherein the test apparatus includes a formulation attachment.

With further reference to FIG. 11, another unique aspect of the present invention is a formulation attachment 95 that can be connected to the test cup 85 to test the effects of additives or the like on the frictional and/or wear characteristics of the test balls 73 and 83. The formulation attachment 95 includes an electric pump 96 that pumps the oil or other fluid being tested through a conduit 97 into the test cup 85. The fluid 99 flows through the test cup 85 and out the opening 93, and is returned to a reservoir 100 through a fluid conduit 98. A drain 101 can be used for drain the fluid 99 from the reservoir 100 upon completion of the test.

The formulation attachment 95 and test cup 85 illustrated in FIG. 11 permits testing that would be very difficult if not impossible with conventional four-ball testers. For example, one could allow a given oil formulation to run until the friction or the conductivity or the impedance or other measured characteristic is stabilized, and then add a known amount of additive 102 to the reservoir 100 and monitor the change in the measured characteristic. The present invention is advantageous because the results of the addition of the additive are the only changes in the test conditions, and not the result of other test variability. Also, the present invention offers substantial time savings because several tests can be run without disassembling, reassembling, cleaning, etc. Also, the run-in time associated with reconfigurations required with prior four-ball testers can also be eliminated.

Figure 12:
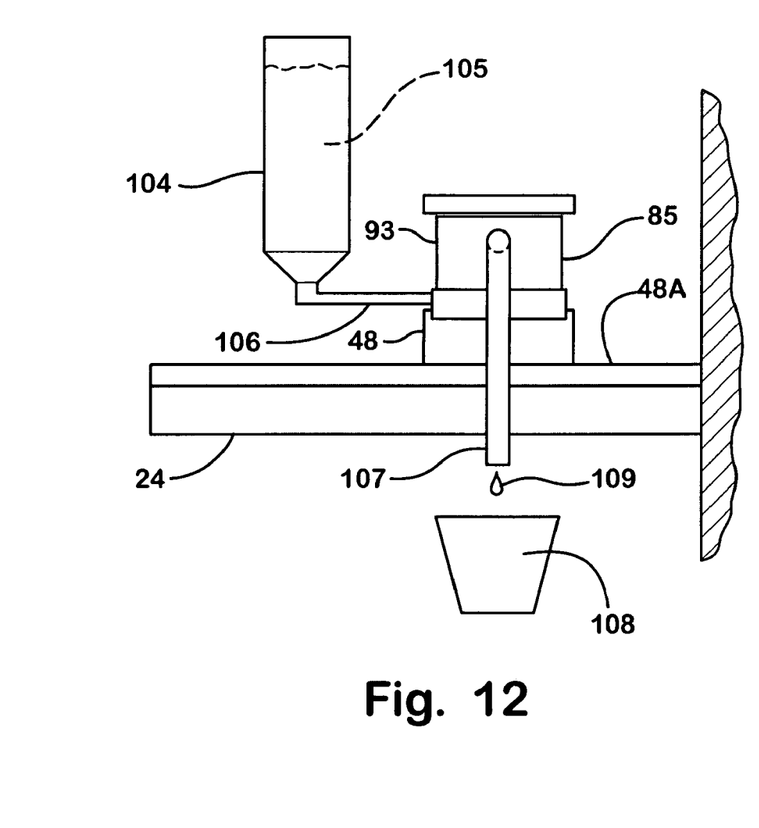
FIG. 12 is a partially schematic view of the four-ball test apparatus including a flow-through testing attachment.

With further reference to FIG. 12, the test cup 85 can also be utilized to conduct flow-through testing in a manner that would be difficult or impossible with conventional four-ball test apparatus configurations. A reservoir 104 contains test fluid 105, and a conduit 106 is connected to the test cup 85. The fluid to be tested 105 flows through the test cup 85, and exits through a second fluid conduit 107, and the exiting fluid 109 is collected in a container 108. During testing, once a run-in has occurred with a standard lubricant having known friction or other characteristics, a first sample of fluid having unknown lubrication characteristics can be added to the reservoir 104. The first sample will flow into the test cup 85 displacing the run-in fluid, permitting testing of the newly-added first sample fluid having unknown characteristics. As the fluid 105 in reservoir 104 flows through test cup 85, the level of the fluid 105 eventually reaches the same height as outlet opening 93, and stabilizes at this level. This ensures that the test cup 85 is not emptied of test fluid during the test. After adding the first sample, another sample can then be added to displace the first sample in the test cup 85, and this process can be repeated to test as many samples as needed. If required for a particular test, a reference lubricant having known characteristics could be run to determine if the test conditions are still within predefined limits. Additional samples could then be tested if the test conditions are still within the predefined limits. A reference lubricant can also be tested after testing of the unknown fluid is completed to ensure that the test conditions have not changed during the course of testing due to additional wear on the test balls or the like. The arrangement illustrated in FIG. 12 for flow-through testing has numerous advantages including speed, because only one run-in for many samples is required. Also, the accuracy is improved because the samples are being compared under substantially identical conditions.

In addition to the advantages discussed above, the four-ball test apparatus 20 of the present invention also permits measurement of conductivity. The wear scar diameter and the deposits that form around the wear scar in the test balls provides useful information concerning a lubricant. However, the electrical resistance or impedance or capacitance provides valuable information concerning whether or not the test balls are making metal to metal contact, or if there might be some degree of separation by way of a very thin film of an insulating, organic nature. All of these can be measured with relative ease utilizing the four-ball test apparatus 20 of the present invention. The test cup is fixed so any required wiring can attached directly to the cup. The shaft of the motor can be readily fitted with a high quality slip ring to complete the circuit.

Figure 13:
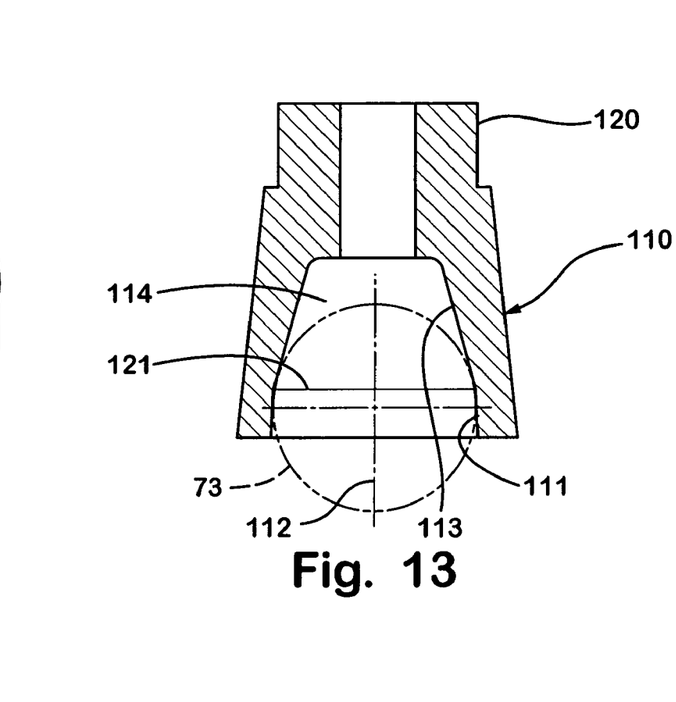
FIG. 13 is a cross-sectional view of a ball chuck that may be utilized with the four-ball test apparatus.

With further reference to FIG. 13, another aspect of the present invention is a chuck 110 that can be utilized to secure the upper test ball to the spindle during testing. Existing chucks utilize slots forming "arms" that flex somewhat upon insertion of the test ball. In addition to the four-ball friction wear tests, extreme pressure tests are also sometimes run. During extreme pressure testing, the final load is a weld load, which means a load that is so high that the four test balls are frictionally welded together. During such extreme pressure testing, the upper test ball often slips or becomes welded to the chuck, or otherwise damages the chuck in conventional chuck designs.

In contrast to such conventional chucks, the chuck 110 of the present invention illustrated in FIG. 13 includes an inner surface 111 having a shallow taper that engages the upper test ball 73. In a preferred embodiment, the tapered wall portion 111 has a two degree taper relative to the center line 112 of the chuck 110. The two degree tapered wall portion tightly contacts the outer surface of test ball 73 and holds the test ball 73 in the chuck if it is raised such that ball 73 is no longer in contact with the lower test balls. An inner surface 113 has a taper of fifteen degrees to thereby limit the travel of the ball 73 in the cavity 114 of chuck 110, and thereby prevent the test ball 73 from becoming wedged too tightly. Although the preferred taper for the wall section 111 is two degrees, a five degree taper, or any taper generally between four and seven degree would hold the test ball 73 during testing, but permit release after the test is completed. If the two degree wall portion is eliminated, such that the ball 73 contacts the fifteen degree surface 113 only (see, e.g. FIG. 9), the contact forces are still sufficient to ensure that the ball 73 does not slip in chuck 110 during testing. However, when only a fifteen degree taper is present, the ball 73 will drop out of chuck 110 when the chuck 110 is raised and ball 73 will remain on the lower test balls 83. The tapered wall of the chuck contacts test ball 73 about a substantially continuous line 121. The tapered sidewall may have an angle greater than fifteen degrees, provided that contact line 121 is greater than the contact circle between test ball 73 and lower test balls 83. This ensures that sufficient friction to retain test ball 73 in the cavity of the chuck during testing. In general, any taper angle that provides sufficient friction to prevent rotation of test ball 73 in chuck 110 is suitable. In a preferred embodiment, the chuck 110 is made of a material that is dissimilar from the steel material of the test ball 73 to prevent welding between the test ball and the chuck. Suitable materials include aluminum, bronze, amaloy or other such materials. One example of a preferred material is a ceramic, which prevents welding and provides high wear resistance in situations wherein the ball does slip in the chuck. Another preferred material is tool steel, such as D2. Chuck 110 may be utilized with either four-ball wear test machines or with conventional four-ball extreme pressure test machines, such as those available from Falex Corporation of Chicago, Ill., chuck 110 may include both fifteen and two degree tapered wall portions for either type of testing, or may include only a fifteen degree wall portion for either type of testing. In the embodiment illustrated in FIG. 9, the tapered sidewall 113 is formed in the end of the spindle 46, such that the chuck forms an integral part of spindle 46. Alternately, a standard attachment 120 may be provided to secure the chuck 110 to, for example, a conventional four-ball extreme pressure test machine such as those made by Falex Corporation or others.

The fifteen degree taper provides sufficient friction to ensure that the test ball 73 does not spin within the chuck 110, but permits simple removal of the test ball 73 from the chuck 110. During testing, the top test ball 73 is placed in the cup on top of the lower test balls 83, and the motor/weight assembly 22 is then brought downwardly by operation of lift assembly 25. The chuck 110 automatically engages the top ball 73 and centers the motor/weight assembly 22 on the lower test balls 83 in the test cup. The relatively low taper of the side walls provides sufficient friction during wear or friction testing to prevent sliding of test ball 73 in chuck 110, yet also prevents binding of the upper test ball 73, such that it drops out of the chuck 110 when the motor/weight assembly 22 is lifted utilizing the lift assembly 25. It is anticipated that sufficient force could be utilized with the four-ball test apparatus 20 of the present invention to permit such extreme pressure testing. One example of such a test is ASTM D-2783 "Measurement of Extreme Pressure Properties of Lubricating Fluids (Four Ball Method)".

The four-ball test apparatus of the present invention ensures that all frictional forces measured by the load cell are due to the frictional engagement between the upper test ball 73 and the lower test balls 83, and eliminates potential errors caused by thrust bearings or the like in prior four-ball test arrangements. Furthermore, because the test cup is rigidly clamped, and does not move, various instruments or fluid lines or the like may be connected to the test cup without introducing additional sources of error in the test measurements.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The invention claimed is:

1. A friction test apparatus, comprising:
a support structure;
a receptacle defining a cavity, and wherein the receptacle is configured to hold a test fluid therein when the receptacle is mounted to the support structure, and wherein the receptacle defines first and second openings in fluid communication with the cavity;
at least one upper friction member rotatably coupled to the support structure;
a clamp associated with the receptacle;
at least three lower friction members non-rotatably clamped in the receptacle by the clamp with portions contacting the upper friction member in sliding contact upon rotation of the upper friction member;
first volume of first test fluid disposed in the cavity and covering the portions of the three lower friction members, the first test fluid comprising a lubricant having a first composition;
a reservoir fluidly coupled to the one of the first and second openings to provide fluid flow from the reservoir through the one opening into the cavity of the receptacle, wherein the reservoir holds a volume of second test fluid at least as large as the first volume, and wherein the second test fluid has a second composition that is different than the first composition.

2. The friction test apparatus of claim 1, including:
a motor providing powered rotational movement of the upper friction member relative to the lower friction members.

3. The friction test apparatus of claim 2, including:
a force-generating mechanism that provides an adjustable force that pushes the upper and lower friction members together.

4. The friction test apparatus of claim 1, wherein:
the upper friction member comprises an upper test ball; and
the lower friction members comprise at least three lower test balls.

5. The friction test apparatus of claim 4, wherein:
the receptacle comprises a test cup having a generally horizontal lower sidewall, and wherein the inner surface of the receptacle is formed by the lower sidewall.

6. The friction test apparatus of claim 5, wherein:
the lower opening comprises an aperture through the lower sidewall.

7. A friction test apparatus, comprising:
a base structure;
a receptacle secured to the base structure, wherein the receptacle includes a sidewall defining an inner surface and an outer surface, the receptacle having first test fluid having a first composition disposed in the receptacle;
at least three lower friction surfaces fixed in the receptacle in contact with the inner surface;
a motor having a rotatable shaft, the motor providing powered rotation of said shaft relative to the at least three lower friction surfaces;
a reservoir having a second test fluid having a second composition that is different than the first composition disposed in the reservoir;
an upper friction surface fixedly positioned on the shaft and slidably engaging the at least three lower friction surfaces in the receptacle upon rotation of the shaft and upper friction surface, the receptacle including a fluid inlet fluidly coupled to the reservoir and a fluid outlet extending from the inner surface to the outer surface and permitting fluid in the receptacle to be removed without disengaging the upper friction surface from the at least three lower friction surfaces.

* * * * *